United States Patent
Kirchberg et al.

(10) Patent No.: US 8,712,115 B2
(45) Date of Patent: Apr. 29, 2014

(54) REAL-TIME VIRTUAL ENDOSCOPY

(75) Inventors: Klaus J. Kirchberg, Princeton, NJ (US); Christine H. Lorenz, Frederick, MD (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 2005 days.

(21) Appl. No.: 11/392,457

(22) Filed: Mar. 29, 2006

(65) Prior Publication Data

US 2006/0235671 A1 Oct. 19, 2006

Related U.S. Application Data

(60) Provisional application No. 60/672,578, filed on Apr. 19, 2005.

(51) Int. Cl.
*G06K 9/00* (2006.01)
*A61B 6/00* (2006.01)

(52) U.S. Cl.
CPC ............ *A61B 6/5223* (2013.01); *A61B 6/5235* (2013.01); *G06K 9/00234* (2013.01)
USPC ............ 382/128; 382/131; 382/132; 382/154

(58) Field of Classification Search
CPC .................. G06T 2211/404; G06T 2211/408; G06T 2211/412; G06T 2211/416; G06T 2211/421; G06T 2211/424; G06T 2211/428; G06T 2211/432; G06T 2211/436; A61B 6/5223; A61B 6/5229; A61B 6/5235; A61B 6/5241; A61B 6/5247; A61B 6/5252; A61B 6/5294; G06K 9/00214; G06K 7/0077; G06K 7/0075; G06K 2207/10012
USPC ......... 382/128, 129, 130, 131, 132, 133, 134, 382/154
See application file for complete search history.

(56) References Cited

U.S. PATENT DOCUMENTS

| | | | | |
|---|---|---|---|---|
| 6,526,163 | B1 * | 2/2003 | Halmann et al. | 382/128 |
| 6,677,697 | B2 * | 1/2004 | Struckmeier et al. | 310/328 |
| 6,898,302 | B1 * | 5/2005 | Brummer | 382/131 |
| 6,919,892 | B1 * | 7/2005 | Cheiky et al. | 345/473 |
| 7,027,054 | B1 * | 4/2006 | Cheiky et al. | 345/473 |
| 2002/0097901 | A1 * | 7/2002 | Xu et al. | 382/131 |
| 2004/0109603 | A1 * | 6/2004 | Bitter et al. | 382/154 |
| 2005/0154291 | A1 * | 7/2005 | Zhao et al. | 600/410 |

OTHER PUBLICATIONS

Andras Kelemen et al. "Elastic Model-Based Segmentation of 3-D Neuroradiological Data Sets", I.E.E.E. Transactions on Medical Imaging, vol. 18, Oct. 1999.*
Xiaodong Tao et al. "Using a Statistical Shape Model to Extract Sulcal Curves on the Outer Cortext of the Human Brain", I.E.E.E. Transactions on Medical Imaging, vol. 21, May 2002.*
AleJandro F. Frangi et al. "Model-Based Quantitation of 3-D Magnetic Resonance Angiographic Images", I.E.E.E. Transactions on Medical Imaging, Oct. 1999.*

* cited by examiner

*Primary Examiner* — Brian Le
(74) *Attorney, Agent, or Firm* — Donald B. Paschburg; F. Chau & Associates, LLC

(57) ABSTRACT

In a method of real-time 3-D visualization and navigation for interventional procedures a position is determined at which data will be acquired, and data is acquired at the position. Features are extracted from the acquired data. A model described by the extracted features is built or updated, wherein updating the model includes calculating at least one acquisition parameter of a set of acquisition parameters. 3-D scenes showing the interior or exterior of one or more organs are displayed using the model or data extracted from the model. A region for updating is determined.

14 Claims, 5 Drawing Sheets

REAL-TIME VIRTUAL ENDOSCOPY

CROSS-REFERENCE TO RELATED APPLICATION

This application claims the benefit of U.S. Provisional Application Ser. No. 60/672,578, filed Apr. 19, 2005 and entitled "Real-time Image-driven Virtual Endoscopy in MRI," the content of which is herein incorporated by reference in its entirety.

BACKGROUND OF THE INVENTION

1. Technical Field

The present invention relates to real-time virtual endoscopy and, more particularly, to methods and systems for real-time 3-D visualization and navigation for interventional procedures.

2. Description of the Related Art

Medical imaging is generally recognized as important for diagnosis and patient care with the goal of improving treatment outcomes. In recent years, medical imaging has experienced an explosive growth due to advances in imaging modalities such as x-rays, computed tomography (CT), magnetic resonance (MR) imaging and ultrasound. These modalities provide noninvasive methods to study internal organs in vivo, producing anatomical and functional image data in 2-D, 3-D or even 4-D (3-D+time). The image data is typically analyzed by a radiologist, who bases his diagnosis on findings in single image slices or in some other graphical representation, e.g., volume rendering.

Advances in magnetic resonance (MR) technology and methodology have triggered research studies in the field of interventional MRI (iMRI). Jolesz provides a general overview of the field of iMRI. Jolesz, F. A., "Interventional and intraoperative MRI: a general overview of the field," In *Journal of Magnetic Resonance Imaging*, January-February 1998, 8(1):3-7. Tsekos provides approaches towards performing real-time coronary MR angiography (MRA) and MR-guided coronary interventions. Tsekos, N. V., Atalar, E., Li, D., Omary, R. A., Serfaty, J. M., Woodard, P. K., "Magnetic Resonance Imaging-Guided Coronary Interventions," In *Journal of Magnetic Resonance Imaging*, 2004, 19(6):734-49. Besides avoiding ionizing radiation exposure of the patient and the physician performing the procedures, performing diagnostic and therapeutic procedures under MRI guidance offers advantages over the current standard of X-ray guidance. For example, high-spatial-resolution MR images, excellent soft-tissue contrast, and selection of arbitrary scan planes in 3-D volumes, without the need to manually reposition the patient or the imaging device, are features that have drawn attention to iMRI.

While not yet applied in the clinical realm, iMRI is an area of intense research. Significant advances have been made in the development of specialized pulse sequences and catheter design and tracking methods. Boll compares pulse sequences for interventional device guidance during magnetic resonance (MR) imaging to evaluate the dependence of sequence selection on the anatomic region of the procedure. Boll, D. T., Lewin, J. S., Duerk, J. L., Aschoff, A. J., Merkle, E. M., "Comparison of MR imaging sequences for liver and head and neck interventions: is there a single optimal sequence for all purposes?" In *Academic Radiology*, May 2004, 11(5):506-15. Buecker provides simultaneous MR real-time active tip tracking and near real-time depiction of the vascular anatomy for percutaneous angioplasty (PTA) of iliac arteries under MR guidance. Buecker, A., Adam, G. B., Neuerburg, J. M., Kinzel, S., Glowinski, A. Schaeffter, T., Rasche, V., van Vaals, J. J. Guenther, R. W., "Simultaneous real-time visualization of the catheter tip and vascular anatomy for MR-guided PTA of iliac arteries in an animal model," In *Journal of Magnetic Resonance Imaging*, August 2002, 16(2): 201-8. Another element of iMRI under development is the visualization and navigation interface. It is desirable to minimize the resources needed for scanner interaction while at the same time providing the most meaningful presentation of the acquired data to the physician in real-time.

Different approaches to MR image visualization for interventional procedures have been proposed. Current techniques include 2-D image display of single or multiple slices in real-time, 2-D projections of MR angiography data and 3-D volume rendering. Zhang provides a target-navigation technique in which the MR scan plane was defined automatically by the invasive device orientation and target tissue location. Zhang, Q., Wendt, M. Aschoff, A., Zheng, L., Lewin, J. Duerk, J., "Active MR guidance of interventional devices with target-navigation," In *Magnetic Resonance in Medical Sciences*, July 2000, 44(1):56-65. Serfaty provides a 2-D projection technique with no section selection. Serfaty, J. M., Atalar, E., Declerck, J., Karmakar, P. Quick, H. H., Shunk, K. A., Heldman, A. W., Yang, X: "Real-Time projection MR angiography: feasibility study," In *Radiology*, October 2000, 217(1):290-5. Guttman provides a system for real-time volume renderings from 2-D multi-slice or 3-D MR pulse sequences. Guttman, M. A., Lederman, R. J., Sorger, J. M., McVeigh, E. R., "Real-time volume rendered MRI for interventional guidance," In *Journal of Cardiovascular Magnetic Resonance*, 2002, 4(4): 431-42.

While virtual endoscopy is generally accepted as a standard diagnostic tool for performing offline procedures, a real-time 3-D first-person view could help a physician to perform interventional procedures. For example, such a view could help monitor stent placement for abdominal aortic aneurysms and to assess and prevent possible tearing of the adjacent wall. Visualizing a catheter tip in a real-time 3-D view could help a physician to guide the device to the target tissue for a trial ablation.

Conventional MR scanning systems are designed to generate diagnostic images using a previously defined set of imaging parameters. Various real-time scanner control systems have been built for different applications. These systems are generally limited to scan plane control and direct parameter manipulation.

SUMMARY OF THE INVENTION

According to an exemplary embodiment of the present invention, a method is provided for real-time 3-D visualization and navigation for interventional procedures. The method includes: determining a position at which data will be acquired; acquiring data at the position; extracting features from the acquired data; building or updating a model described by the extracted features, wherein updating the model includes calculating at least one acquisition parameter of a set of acquisition parameters; displaying 3-D scenes showing the interior or exterior of one or more organs using the model or data extracted from the model; and determining a region for updating.

According to another exemplary embodiment of the present invention, a method is provided for real-time 3-D visualization and navigation for interventional procedures. The method includes: acquiring slice or volume data; extracting boundary locations from the acquired slice or volume data; building or updating a model using the extracted boundary locations, wherein updating the model includes calculating at least one acquisition parameter of a set of acquisition parameters; displaying 3-D scenes using the model or data extracted from the model; and calculating a slice or volume position for updating.

According to an exemplary embodiment of the present invention, a system is provided for real-time 3-D visualization and navigation for interventional procedures. The system comprises: a graphical user interface; an MR scanner in data communication with the graphical user interface, wherein the MR scanner includes a real-time pulse sequence program that allows changing scan parameters during acquisition; and a controller, wherein the controller requests data from the MR scanner, and wherein the controller provides position data and at least one of a set of acquisition parameters to the MR scanner.

According to an exemplary embodiment of the present invention, a system is provided for real-time 3-D visualization and navigation for interventional procedures. The system comprises: an imaging device operable to acquire data and transmit the acquired data; a processor, wherein the processor extracts features from the acquired data and generates a model; and a display device in data communication with the processor, the display being operable to display 3-D scenes showing the interior or exterior of one or more organs using the model or data extracted from the model.

The present invention will become more apparent to those of ordinary skill in the art when descriptions of exemplary embodiments thereof are read with reference to the accompanying drawings.

DETAILED DESCRIPTION OF EXEMPLARY EMBODIMENTS

Figure 1:
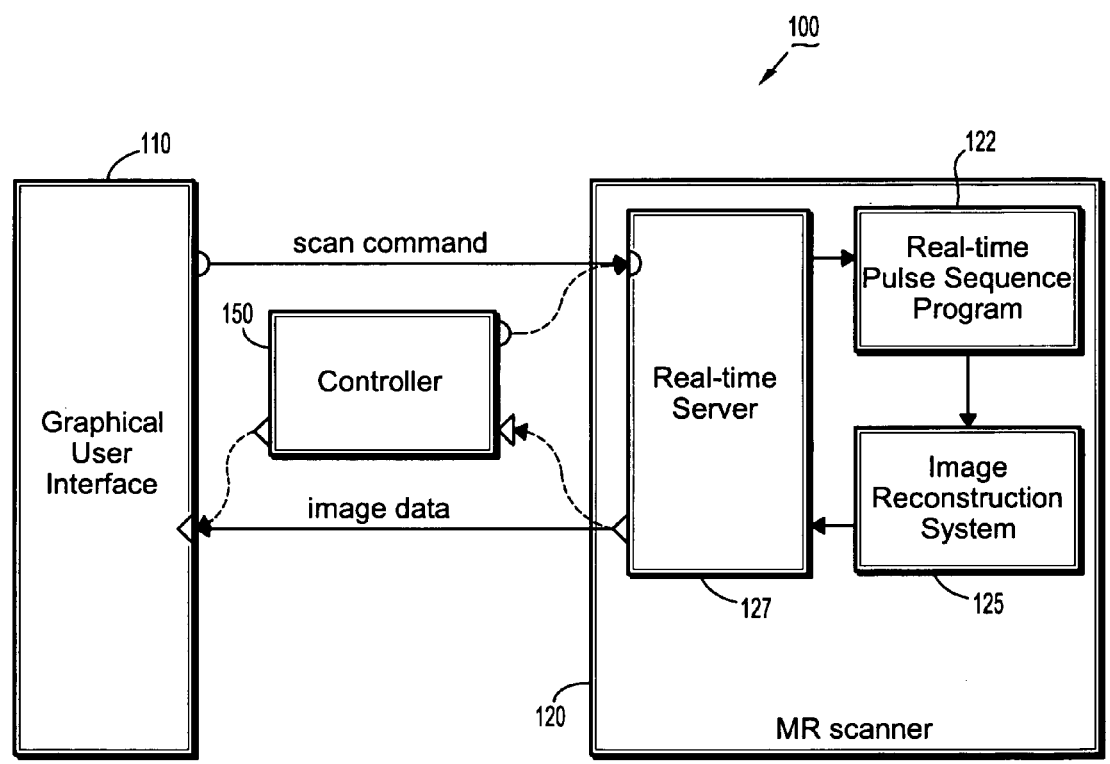
FIG. 1 illustrates a scanning system, according to an exemplary embodiment of the present invention.

Hereinafter, exemplary embodiments of the present invention will be described in detail with reference to the accompanying drawings. Like reference numerals refer to similar or identical elements throughout the description of the figures.

In exemplary embodiments of the present invention, the technical basis for navigation in iMRI is a software and hardware environment for real-time scanner control and interaction. The term "real-time" refers to a level of computer responsiveness that a user senses as sufficiently immediate or that enables the computer to keep up with some external process (for example, to present visualizations of objects moving across the screen at the same speed that they actually move). Real-time describes a human rather than a machine sense of time.

It is to be understood that the present invention may be implemented in various forms of hardware, software, firmware, special purpose processors, or a combination thereof. In one embodiment, the present invention may be implemented in a client-server structure. FIG. 1 illustrates a scanning system, according to an exemplary embodiment of the present invention.

Referring to FIG. 1, the scanning system 100 includes a graphical user interface 110, controller 150, and MR scanner 120 in data communication with the graphical user interface 110. It is to be understood that the scanning system 100 may include a CT scanner in lieu of, or in addition to, the MR scanner 120, and that various imaging modalities are suitable for implementing the invention. The controller 150 requests data from the MR scanner 120, and the controller 150 provides position data and at least one acquisition parameter of a set of acquisition parameters to the MR scanner 120. The set of acquisition parameters includes, but is not limited to, position data, orientation data, timing data, and MR contrast data.

As shown in FIG. 1, the MR scanner 120 includes the real-time server 127, the real-time pulse sequence program 122, and the image reconstruction system 125. As discussed later in this disclosure, the real-time pulse sequence program 122 allows changing scan parameters during acquisition.

The real-time server 127 is an application running on, for example, the MR scanner's host computer. The real-time server 127 provides an interface to communicate with the scanner. External applications can connect from personal computers (PCs) in the same local network to send scan commands and receive the corresponding reconstructed image data. For example, it provides a socket connection that can receive scan commands from an external PC in the same network. Scan commands contain information such as scan position, slice orientation, pulse sequence parameters, a network address defining the location to which the image data is sent, etc. In an exemplary embodiment of the present invention, all network communication is done via TCP/IP sockets.

A dedicated interactive real-time pulse sequence program 122 is continuously running on the scanner 120 during a procedure. The sequence is capable of changing certain sequence parameters and scan position and orientation during runtime and reconstructing images in real-time. For example, real-time pulse sequence program 122 receives scan parameters from the real-time server 127 and applies it to the next slice to be scanned.

After the scanner system has finished reconstructing the images from the acquired data, the image reconstruction system 125 sends the data to the network socket defined in the scan command. In addition, the image server sends actual position data and orientation as well as phase encoding and readout direction along with the image—these parameters define the correspondence between image pixel coordinates and real world coordinates.

To interactively manipulate and visualize the scan planes, according to an exemplary embodiment of the present invention, a graphical user interface 110 communicates with the scanner 120. In an exemplary embodiment of the present invention, the graphical user interface 110 displays the scanned slices in a 3-D renderer. The graphical user 100 interface may comprise one or more 2-D or 3-D scene visualizations of image data, model and/or data extracted from the model, and graphical controls to interact with the scenes.

For example, the scanning system 100 can be used to develop a scan automation module that creates a 3-D model of a tubular structure. The model can be used, for example, to create a virtual endoscopic view inside the human aorta. In this example, a seed point inside the structure and an initial view direction is given a priori.

Segmentation can be carried out by a thresholding technique or by a more advanced contour finding procedure, e.g., using level-sets, or by any suitable technique. An implementation of the first approach is described below.

Let $S^i = S(c^i, n^i, t^i, p)$ be the reconstructed image acquired at slice center position $c^i$ with unit normal direction $n^i$. $t^i$ denotes the time point of acquisition, and p denotes the remaining sequence parameters which are kept constant during the procedure. Given some initial position $c^0$ and normal direction $n^0$, the first slice is acquired and segmented.

The segmentation procedure requires a seed point V (image coordinates) inside the structure (e.g., the aorta) for initialization. The slice center positions $c^i$ are chosen to be inside the aorta, so V can be set to the center of the image. An ordered set of points $V_k$, k=1 ... M on the outline of the vessel in slice i is then found by $$A_k^i = \arg \min_{A \in A(S^i, V^i, \theta)} \|A - V\|, k = 1 \ldots M$$

with $$A_k(S, V, \theta) = \left\{ X : X = \left\lfloor V + \alpha \begin{pmatrix} \cos\phi_k \\ \sin\phi_k \end{pmatrix} + \begin{pmatrix} 0.5 \\ 0.5 \end{pmatrix} \right\rfloor, \alpha > 0, S_X < \theta \right\}$$

$$\theta_k = 2\pi \frac{k-1}{N}.$$

Here, $S_x$ denotes the gray value of the pixel at position x in the image and θ represents a threshold distinguishing the bright aorta from the background. The choice for the number of segmentation points M is a tradeoff between computational complexity for both segmentation and later rendering and accuracy of the model. To capture the border at pixel accuracy, we can set M≅πd, where d is the approximate diameter of the vessel in pixel.

The result of the segmentation process is a number of image points $U_k^i$, k=1 ... N describing the border of the aorta in a clockwise fashion for each scanned slice $S_i$.

Using this approach, to provide a high spatial resolution in radial direction, the scan plane should be close to perpendicular to the structure's centerline. The scan path planning procedure achieves this by estimating a local linear approximation of the centerline and extrapolating the new scan plane's normal direction. The center of mass $C^i$ of the aorta's cross section is approximated by $$C^i = \frac{1}{N} \sum_{k=1}^{N} U_k^i.$$

With the known image-to-world coordinate transformation $T^i$, the center position in world coordinates is given by $c^i = T^i(C^i)$. The new scan slice position is extrapolated as $$x^{i+1} = c^i + \sigma \frac{c^i - c^{i-1}}{|c^i - c^{i-1}|},$$

where σ denotes the step size between two consecutive slices in world coordinates. This approach tries to center the aorta in the upcoming image.

The new slice normal direction is then determined by $$n^{i+1} = \lambda n^i + (1 - \lambda) \frac{c^i - c^{i-1}}{|c^i - c^{i-1}|},$$

with some attenuation factor 0≤λ≤1, which depends on the expected curvature of the vessel.

The points on the aorta's border as found by the segmentation process are then used to build a geometric 3-D model. Using the known transformation of image coordinates to world coordinates, the 2-D points define the vertices for the model in world coordinates. The mesh is continuously updated as the scan plane advances along the tubular structure.

The methods and systems for real-time 3-D visualization and navigation for interventional procedures, in accordance with exemplary embodiments of the present invention, may be used as techniques for MR-guided interventions in the human aorta. Coarctation (narrowing) and aneurysms (enlargements) are examples of aortic defects that can be treated by minimally invasive catheter based procedures under x-ray or MRI guidance. During the treatment, a stent graft is inserted and deployed at the appropriate position.

Figure 5:
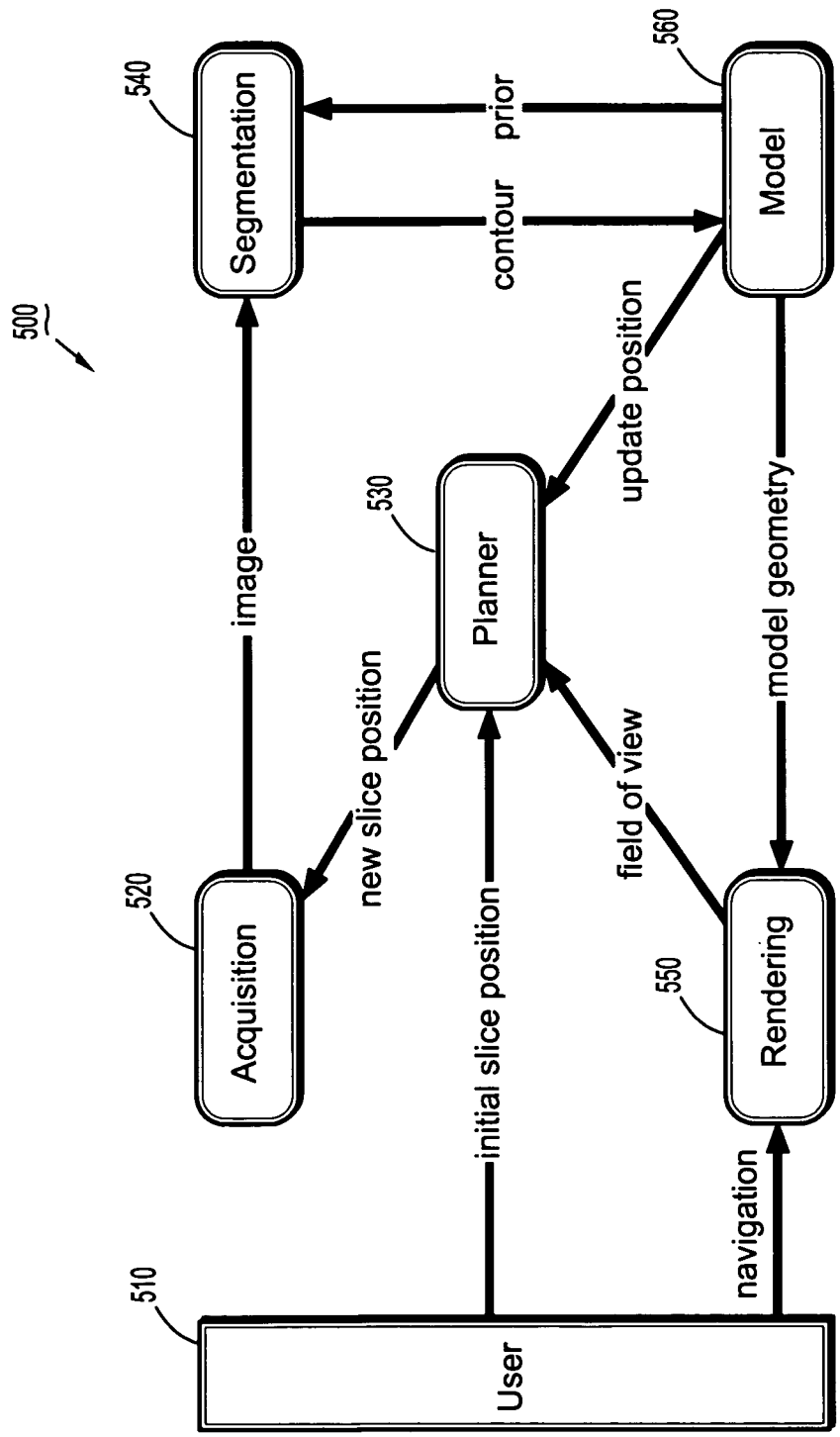
FIG. 5 illustrates a system for real-time 3-D visualization and navigation for interventional procedures, according to an exemplary embodiment of the present invention.

The system for real-time interaction with the MR scanner includes means for changing slice position and orientation during scanning and communication means for sending the resulting image data to the processing system. FIG. 5 illustrates a system for real-time 3-D visualization and navigation for interventional procedures, according to an exemplary embodiment of the present invention. Hereinafter the data flow will be described with reference to FIG. 5.

Image slices are acquired by the acquisition component 520 perpendicular to the aorta's main axis. The scanned images are first subject to segmentation 540. Here, points on the aortic wall are extracted and their 3-D position is determined by applying the (known) transformation of the image slice. Optionally the segmentation 540 can be initialized by prior shape knowledge gained from the current model 560. After segmentation 540, the 3-D coordinates of the contour points are added to the cloud of data points. An optimization is continuously fitting and updating the aorta model 560 to best match the point cloud. The coherence information of contour points within one slice is not necessary for the model 560, thus leading to a more general system that can easily be extended to other organs.

The geometric model 560 is then used by the rendering component 550 to display one or more 3-D views of the interior or exterior of the organ. Optional anatomical, functional data or reference data can be overlayed. The user 510 can then navigate through the scene by changing position and orientation of the virtual camera defining the view created by the rendering component 550.

Using the shape knowledge from the current model 560 and/or the current field of view in the 3-D scene, the planner component 530 requests new image slices or volumes from the acquisition component 520.

Figure 2:
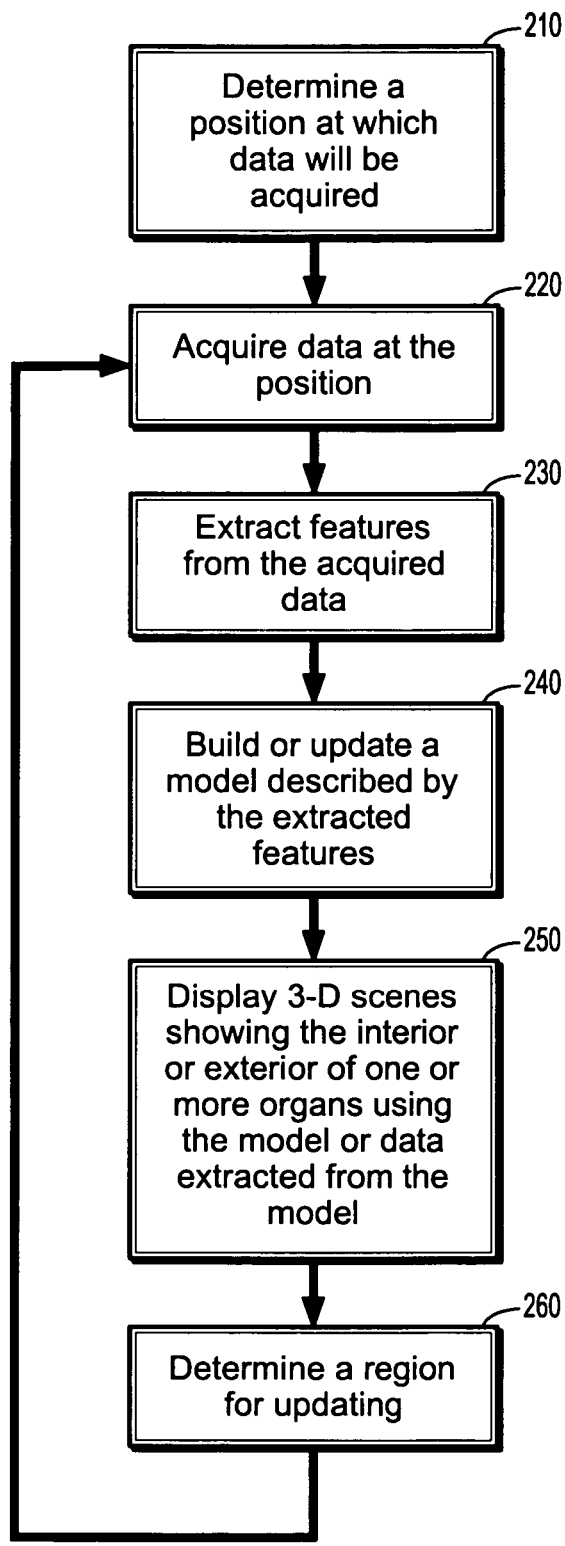
FIG. 2 is a flowchart showing a method of real-time 3-D visualization and navigation for interventional procedures, according to an exemplary embodiment of the present invention.

FIG. 2 is a flowchart showing a method of real-time 3-D visualization and navigation for interventional procedures, according to an exemplary embodiment of the present invention. Referring to FIG. 2, in a step 210, a position is determined at which data will be acquired. Determining a position where data is acquired can be done either automatically or interactively.

In a step 220, data is acquired at the position. In an exemplary embodiment of the present invention, acquiring data comprises obtaining anatomical data and/or functional data derived from at least one imaging modality. For example, acquiring data may comprise performing an MR scan at the position to obtain anatomical data and/or functional data.

Features are extracted from the acquired data, in a step 230. Extracting features may comprise finding boundaries between a plurality of regions in the image. For example, the regions may correspond to the interior or the surface of an organ. As used herein, "organ" refers to an organ or anatomical structure. Extracting features may comprise segmenting the data.

In a step 240, a model described by the extracted features is built or updated. Updating the model includes calculating at least one acquisition parameter of a set of acquisition parameters. The set of acquisition parameters includes, but is not limited to, position data, orientation data, timing data, and MR contrast data. It is contemplated that the data can be used directly for rendering without building a model.

In a step 250, 3-D scenes are displayed showing the interior or exterior of one or more organs using the model or data extracted from the model. In an exemplary embodiment of the present invention, displaying 3-D scenes includes allowing a user to interact with the 3-D scenes.

In a step 260, a region for updating is determined. In an exemplary embodiment of the present invention, the 3-D scenes are continuously updated or real-time updated using the region for updating, on-line MR acquisition, segmentation, and/or modeling.

In an exemplary embodiment of the present invention, a real-time pulse sequence program that allows changing scan parameters during acquisition is provided.

Figure 3:
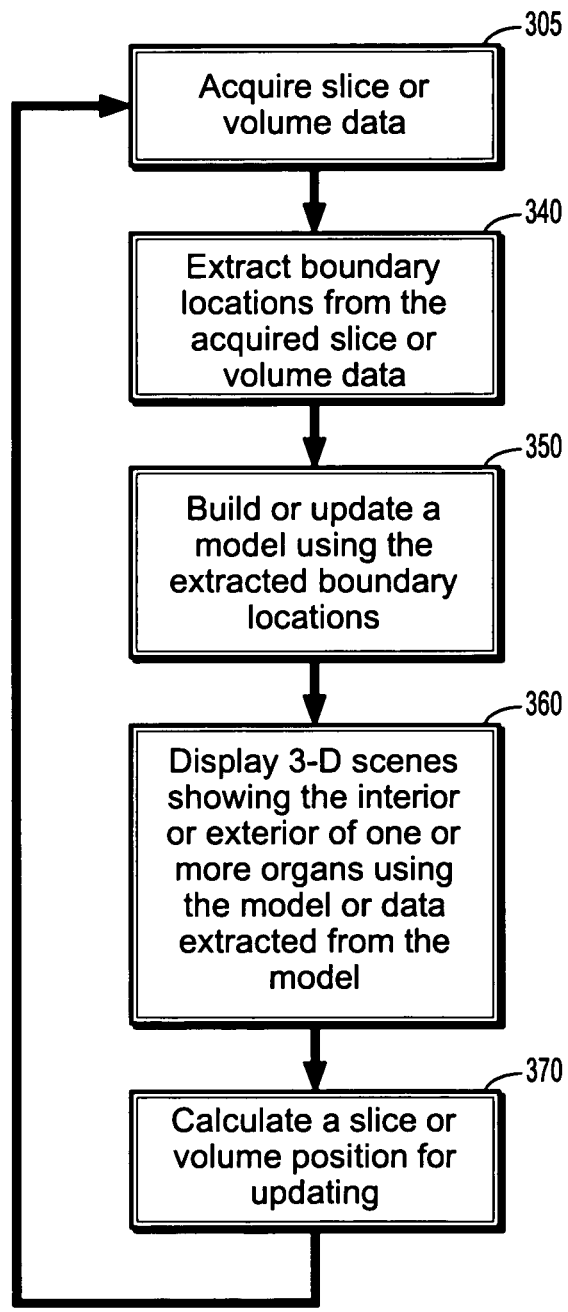
FIG. 3 is a flowchart showing a method of real-time 3-D visualization and navigation for interventional procedures, according to an exemplary embodiment of the present invention.
Figure 4:
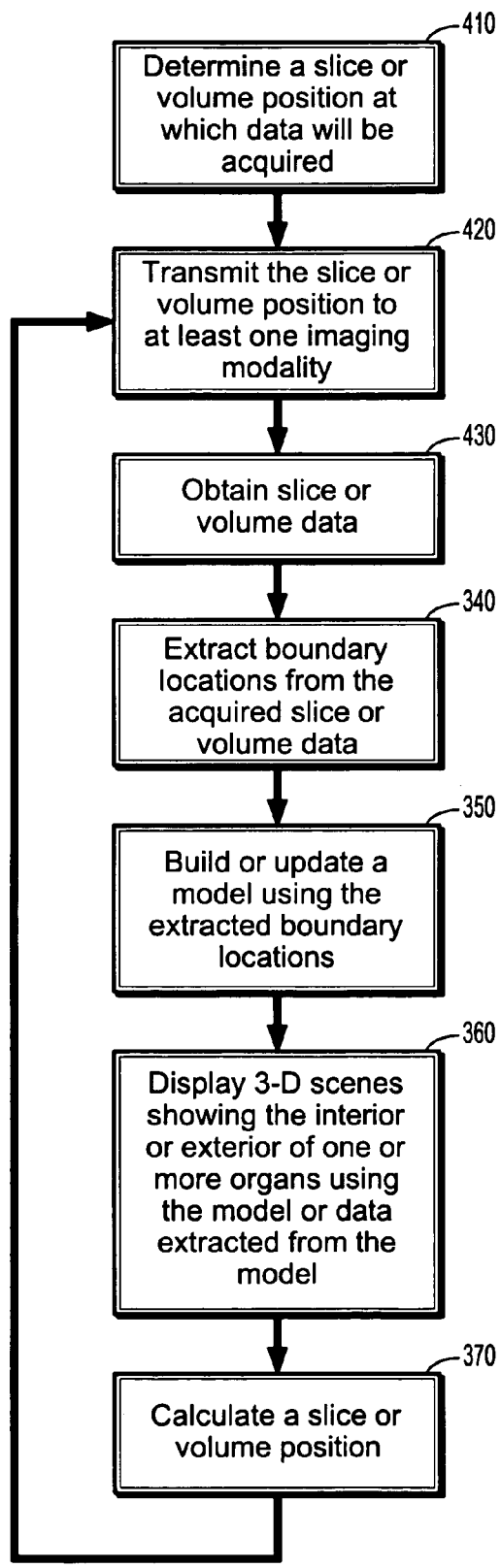
FIG. 4 is a flowchart showing a method of real-time 3-D visualization and navigation for interventional procedures, according to an exemplary embodiment of the present invention.

FIGS. 3 and 4 are flowcharts showing methods of real-time 3-D visualization and navigation for interventional procedures, according to exemplary embodiments of the present invention. Referring to FIG. 3, in a step 305, slice or volume data is acquired. For example, acquiring slice or volume data may comprise the steps of: determining a slice or volume position at which data will be acquired 410; transmitting the slice or volume position to at least one imaging modality 420; and obtaining slice or volume data derived from the at least one imaging modality 430, as shown in FIG. 4. The acquired slice or volume data may comprise pixels or voxels.

In a step 340, boundary locations are extracted from the acquired slice or volume data. This may involve segmenting the acquired slice or volume data. A segmentation is specified by associating the pixels or voxels with either one of a plurality of regions. In an exemplary embodiment of the present invention, extracting boundary locations comprises determining locations in the image that are between a plurality of regions.

In a step 350, a model is built or updated using the extracted boundary locations. Updating the model includes calculating at least one acquisition parameter of a set of acquisition parameters. The set of acquisition parameters includes, but is not limited to, position data, orientation data, timing data, and MR contrast data. Building a model may include using prior knowledge of anatomy and/or anatomical function. It is contemplated that the data can be used directly for rendering without building a model.

In a step 360, 3-D scenes showing the interior or exterior of one or more organs are displayed using the model or data extracted from the model.

In a step 370, a slice or volume position for updating is calculated. In an exemplary embodiment of the present invention, the 3-D scenes are continuously updated or real-time updated using the slice or volume position for updating, on-line MR acquisition, segmentation, and/or modeling.

In an exemplary embodiment of the present invention, a real-time pulse sequence program that allows changing scan parameters during acquisition is provided.

Hereinafter, a system for real-time 3-D visualization and navigation for interventional procedures, in accordance with an exemplary embodiment of the present invention, will be described. The system includes an imaging device and a processor, and a display device in data communication with the processor.

The imaging device is operable to acquire data and transmit the acquired data. The imaging device comprises at least one imaging modality. For example the imaging device may be an MR scanner.

The processor extracts features from the acquired data and generates a model; and a display device in data communication with the processor. The display is operable to display 3-D scenes using the model or data extracted from the model. The model may comprise a model of anatomy, function, shape, deformation, and/or appearance. The 3-D scenes can include a view of the interior of the model.

It is to be understood that the present invention may be implemented in various forms of hardware, software, firmware, special purpose processors, or a combination thereof. In one embodiment, the present invention may be implemented in software as an application program tangibly embodied on a program storage device. The application program may be uploaded to, and executed by, a machine comprising any suitable architecture.

It is to be further understood that, because some of the constituent system components and method steps depicted in the accompanying figures may be implemented in software, the actual connections between the system components (or the process steps) may differ depending upon the manner in which the present invention is programmed. Given the teachings of the present invention provided herein, one of ordinary skill in the related art will be able to contemplate these and similar implementations or configurations of the present invention.

Hereinafter, a computer readable medium including computer code for real-time 3-D visualization and navigation for interventional procedures, in accordance with an exemplary embodiment of the present invention, will be described. The computer readable medium comprises: computer code for determining a position at which data will be acquired; computer code for acquiring data at the position; computer code for extracting features from the acquired data; computer code for building a model described by the extracted features; computer code for displaying 3-D scenes showing the interior or exterior of one or more organs using the model or data extracted from the model; and computer code for determining a region for updating.

What is claimed is:

1. A method of real-time 3-D visualization and navigation for interventional procedures, comprising the steps of:
   determining a position at which data will be acquired;
   acquiring image data at the position;
   extracting features from the acquired image data, the features corresponding to boundaries between regions;
   building a model described by the extracted features;
   displaying a 3-D scene in real-time showing one or more of the regions using the model or data extracted from the model;
   allowing a user to navigate through the displayed 3-D scene by changing the position and an orientation of a virtual camera of the 3-D scene display; and
   updating at least one of the regions by calculating at least one acquisition parameter of a set of acquisition parameters and controlling a target acquisition area of a scanner acquiring the image data by the at least one acquisition parameter based on the changed position and orientation of the virtual camera of the scanner acquiring the data.

2. The method of claim 1, wherein determining a position comprises either one of automatically determining a position where data is acquired or interactively determining a position where data is acquired.

3. The method of claim 1, wherein acquiring image data comprises obtaining at least one of anatomical data or functional data derived from at least one imaging modality.

4. The method of claim 1, wherein extracting features comprises finding boundaries between a plurality of regions in the image.

5. The method of claim 1, wherein displaying 3-D scenes includes the allowing the user to interact with the 3-D scenes being captured by the scanner in real-time.

6. The method of claim 1, wherein the set of acquisition parameters comprises position data, orientation data, timing data, and MR contrast data.

7. The method of claim 1, further comprising continuously updating or real-time updating the 3-D scenes using at least one of the region for updating, on-line MR acquisition, segmentation, or modeling.

8. The method of claim 1, further comprising providing a real-time pulse sequence program that allows changing scan parameters during acquisition.

9. A non-transitory computer readable medium having program instructions stored thereto for implementing the method claimed in claim 1 when executed in a digital processing device.

10. A non-transitory computer readable medium having program instructions stored thereto for implementing a method of real-time 3-D visualization and navigation for interventional procedures when executed in a digital processing device, the method comprising:

providing a real-time pulse sequence program that allows changing scan parameters during acquisition;

acquiring slice or volume data;

extracting boundary locations from the acquired slice or volume data;

updating a model using the extracted boundary locations, wherein updating the model includes calculating at least one acquisition parameter of a set of acquisition parameters and controlling a scanner acquiring the data by the at least one acquisition parameter to update a slice or volume position;

displaying 3-D scenes in real-time using the model or data extracted from the model;

allowing a user to navigate through the displayed 3-D scene by changing a position and an orientation of a virtual camera of the 3-D scene display; and controlling a target acquisition area of the scanner acquiring the slice or volume data based on the changed position and orientation of the virtual camera of the 3-D scene display.

11. The method of claim 10, wherein acquiring slice or volume data comprises:

transmitting the slice or volume position to at least one imaging modality; and obtaining the slice or volume data derived from the at least one imaging modality.

12. The method of claim 10, wherein building a model includes using prior knowledge of at least one of anatomy or function.

13. The method of claim 10, wherein the set of acquisition parameters comprises position data, orientation data, timing data, and MR contrast data.

14. The method of claim 10, further comprising continuously updating or real-time updating the 3-D scenes using at least one of the slice or volume position, on-line MR acquisition, segmentation, or modeling.

* * * * *